(12) United States Patent
Swanson et al.

(10) Patent No.: US 7,766,906 B2
(45) Date of Patent: Aug. 3, 2010

(54) OCCLUSION APPARATUS

(75) Inventors: David K. Swanson, Campbell, CA (US); David L. McGee, Sunnyvale, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 442 days.

(21) Appl. No.: 11/207,234

(22) Filed: Aug. 19, 2005

(65) Prior Publication Data
US 2007/0043349 A1 Feb. 22, 2007

(51) Int. Cl.
*A61B 18/14* (2006.01)
(52) U.S. Cl. .................................................. 606/41
(58) Field of Classification Search ............. 606/41, 606/32–50
See application file for complete search history.

(56) References Cited

U.S. PATENT DOCUMENTS

| | | | |
|---|---|---|---|
| 5,433,708 A * | 7/1995 | Nichols et al. | 604/113 |
| 5,769,790 A | 6/1998 | Watkins et al. | |
| 5,913,856 A * | 6/1999 | Chia et al. | 606/41 |
| 5,919,200 A | 7/1999 | Stambaugh et al. | |
| 5,944,738 A | 8/1999 | Amplatz et al. | |
| 6,007,514 A | 12/1999 | Nita | |
| 6,024,718 A | 2/2000 | Chen et al. | |
| 6,378,501 B1 | 4/2002 | Hisato et al. | |
| 6,458,100 B2 | 10/2002 | Roue et al. | |
| 6,482,224 B1 | 11/2002 | Michler et al. | |
| 6,522,930 B1 * | 2/2003 | Schaer et al. | 607/101 |
| 6,539,265 B2 | 3/2003 | Medhkour et al. | |
| 6,575,967 B1 * | 6/2003 | Leveen et al. | 606/41 |
| 6,645,225 B1 | 11/2003 | Atkinson | |
| 6,650,923 B1 | 11/2003 | Lesh et al. | |
| 6,716,184 B2 | 4/2004 | Vaezy et al. | |
| 6,755,790 B2 | 6/2004 | Stewart et al. | |
| 6,776,784 B2 | 8/2004 | Ginn | |
| 6,923,805 B1 | 8/2005 | LaFontaine et al. | |
| 7,104,989 B2 * | 9/2006 | Skarda | 606/41 |
| 2002/0183787 A1 | 12/2002 | Wahr et al. | |
| 2003/0004505 A1 | 1/2003 | Bencini et al. | |
| 2003/0045901 A1 | 3/2003 | Opolski | |
| 2003/0050665 A1 | 3/2003 | Ginn | |

(Continued)

FOREIGN PATENT DOCUMENTS

WO WO 2004086944 10/2004

(Continued)

OTHER PUBLICATIONS

International Search Report, Nov. 17, 2006, 6 pgs.

*Primary Examiner*—Michael Peffley
*Assistant Examiner*—Ronald Hupczey, Jr.
(74) *Attorney, Agent, or Firm*—Brooks, Cameron & Huebsch, PLLC (57) ABSTRACT

Methods, apparatus, and systems for occluding a tissue opening are provided. One embodiment includes a catheter having an elongate body and a first lumen to direct hypertonic saline through an opening in the lumen to tissue of a fossa ovalis. The embodiment includes a radiofrequency (RF) electrode coupled to the elongate body proximal a distal end of the elongate body. The RF electrode can emit RF energy to the tissues of the passage and the hypertonic saline can facilitate a distribution of the RF energy along the tissue to fuse the tissue of the passage.

3 Claims, 10 Drawing Sheets

U.S. PATENT DOCUMENTS

| | | |
|---|---|---|
| 2003/0144694 A1 | 7/2003 | Chanduszko et al. |
| 2003/0181945 A1 | 9/2003 | Opolski et al. |
| 2003/0191495 A1 | 10/2003 | Ryan et al. |
| 2003/0208232 A1 | 11/2003 | Blaeser et al. |
| 2003/0225421 A1 | 12/2003 | Peavey et al. |
| 2004/0073242 A1 | 4/2004 | Chanduszko |
| 2004/0087968 A1 | 5/2004 | Core |
| 2004/0092973 A1 | 5/2004 | Chanduszko |
| 2004/0093017 A1 | 5/2004 | Chanduszko |
| 2004/0098121 A1 | 5/2004 | Opolski |
| 2004/0127855 A1 | 7/2004 | Core |
| 2004/0127917 A1 | 7/2004 | Ginn |
| 2004/0133236 A1 | 7/2004 | Chanduszko |
| 2004/0176788 A1 | 9/2004 | Opolski |
| 2004/0176797 A1 | 9/2004 | Opolski |
| 2004/0176799 A1 | 9/2004 | Chanduszko et al. |
| 2004/0193147 A1 | 9/2004 | Malecki et al. |
| 2004/0230185 A1 | 11/2004 | Malecki et al. |
| 2004/0243122 A1 | 12/2004 | Auth et al. |
| 2004/0267191 A1 | 12/2004 | Gifford, III et al. |
| 2004/0267306 A1 | 12/2004 | Blaeser et al. |
| 2005/0021016 A1 | 1/2005 | Malecki et al. |
| 2005/0034735 A1 | 2/2005 | Deem et al. |
| 2005/0043759 A1 | 2/2005 | Chanduszko |
| 2005/0055019 A1 | 3/2005 | Skarda |
| 2005/0059983 A1 | 3/2005 | Opolski et al. |
| 2005/0065506 A1 * | 3/2005 | Phan ............................ 606/41 |
| 2005/0070923 A1 | 3/2005 | McIntosh |
| 2005/0070952 A1 | 3/2005 | Devellian |
| 2005/0080406 A1 | 4/2005 | Malecki et al. |
| 2005/0080430 A1 | 4/2005 | Wright, Jr. et al. |
| 2005/0085843 A1 | 4/2005 | Opolski et al. |
| 2005/0101984 A1 | 5/2005 | Chanduszko et al. |
| 2005/0131401 A1 | 6/2005 | Malecki et al. |
| 2005/0131460 A1 | 6/2005 | Gifford, III et al. |
| 2006/0079870 A1 | 4/2006 | Barry |
| 2006/0122680 A1 * | 6/2006 | Auth et al. .................. 607/122 |

FOREIGN PATENT DOCUMENTS

WO    WO 2004086944 A2 *    10/2004

* cited by examiner

OCCLUSION APPARATUS

FIELD OF THE INVENTION

The present disclosure relates generally to apparatus, systems, and methods for use in the human body, more particularly to apparatus, systems, and methods to occlude a patent foramen ovale.

BACKGROUND

The human heart is divided into four chambers. These include the right atrium, the right ventricle, the left atrium, and the left ventricle. The right atrium and right ventricle are divided from the left atrium and left ventricle by a muscular wall called the septum. The atrial septum is the wall separating the atria and the ventricular septum is the wall separating the ventricles.

On the right atrial side of the atrial septum is a thin walled recessed portion of septal tissue called the fossa ovalis. In the heart of a fetus, the fossa ovalis is open and is called a foramen ovale. The foramen ovale is a small hole located in the atrial septum that is used during fetal circulation to speed up the travel of blood through the heart. Thus, blood can travel from the veins to the right side of the fetal heart and cross to the left side through the foramen ovale, bypassing the fetus's lungs.

Normally, the foramen ovale closes at birth when increased blood pressure on the left side of the heart forces the opening close. If the atrial septum does not close properly the resulting condition is called a patent foramen ovale (PFO). The PFO condition works like a valve, opening when increased pressure in the chest occurs. In some instances, this increased pressure can be caused by a valsalva maneuver. The valsalva maneuver can occur when people strain while having a bowel movement, a cough, or a sneeze.

During a valsalva maneuver, blood pressures within the right atrium can increase to a point at which blood may travel from the right atrium to the left atrium. If there is a clot or particles in the blood traveling in the right side of the heart, it can cross the PFO and enter the left atrium. The clot or particles can then travel out of the heart and to the brain (causing a stroke) or into a coronary artery (causing a heart attack).

DETAILED DESCRIPTION

Embodiments of the present invention are directed to methods, apparatus, and systems for occluding a patent foramen ovale (PFO) at the location of the fossa ovalis of the heart. As used herein, a PFO is an opening in the atrial septum defined by tissues of the septum secundum (SS) and septum primum (SP). In the various embodiments described, the SS can be referred to as thick tissue and the SP can be referred to as thin tissue. In addition, when referring to tissue adjacent the fossa ovalis, that tissue can include SS and SP.

In various embodiments, occluding the PFO can be accomplished through the use of a catheter delivered to the left atrium. In various embodiments, once the catheter is properly positioned within the left atrium, an occlusion apparatus coupled to the catheter can be manipulated so as to bring the tissue adjacent the fossa ovalis together.

In various embodiments, an area of tissue at and proximal to the area in which the tissues are brought together can be covered with hypertonic saline. In various embodiments, an RF electrode can be used to conduct RF energy through the hypertonic saline covering the brought together tissue and to facilitate a distribution of the RF energy along the covered tissue to fuse the tissue together and occlude the PFO.

In various embodiments, a system can include the catheter having the occlusion apparatus extendably positioned within the catheter. The system can also include a targeting device configured to locate and/or create a target for the RF energy to be delivered and to monitor the delivery of the RF energy and hypertonic saline.

As will be discussed herein, in the various embodiments of the present disclosure, tissues (e.g., SS and SP) can be brought together before, during, and/or after applying energy to the tissues. The use of RF energy on tissue of the passage denatures the collagen in the tissue. Tissue that undergoes denaturization will tend to renature. If tissues brought together remain in contact while they renature, the collagen in the tissues brought together will effectively combine to fuse the once separated tissues together.

The method, apparatus, and system embodiments described herein are illustrated with reference to fusing tissue adjacent the fossa ovalis (i.e., fusing tissue of the SS and SP together) to occlude a PFO. However, the method, apparatus, and system embodiments can also be used to fuse other tissues and thus, occlude other openings or treat other defects. For example, using the various method, apparatus, and system embodiments described herein, various defective occlusions such as patent ductus arteriosus (PDA), which is a tubular communication between the pulmonary artery and the aorta, ventricular septal defects (VSDs), and atrial septal defects (ASDs) can be treated.

Figure 1:
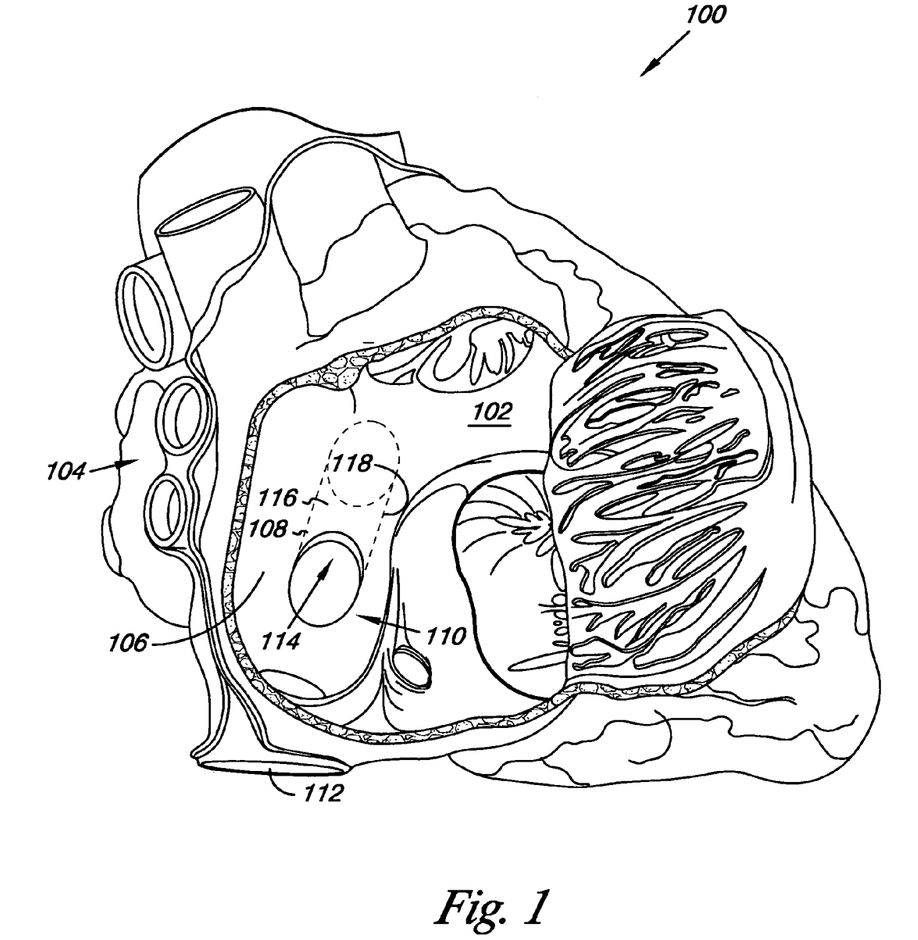
FIG. 1 illustrates a perspective view of the heart is shown.

In FIG. 1, a right lateral view of the heart 100 is shown with an opened right atrium 102. The heart 100 is divided into four chambers, which are referred to herein as the right atrium 102, a right ventricle, a left atrium 104 and a left ventricle. Heart 100 also includes a septal wall 106 that divides the four chambers of the heart. The portion of the septal wall dividing the left and right atriums 102 and 104 is called the interatrial septum 108. The portion of the septal wall 106 dividing the left and right ventricle is called the ventricular septum.

The fossa ovalis 110 is an oval depression on the septal wall 106 of the interatrial septum 108, and corresponds to the situation of the foramen ovale (i.e., the communication between the right and left atria in the fetal heart). The fossa ovalis 110 is situated at the lower part of the atrial septum 108, above and to the left of the orifice of the inferior vena cava 112.

Patent foramen ovale is a flaplike opening at the location of the fossa ovalis 110 between two membranes or tissues referred to as septum secundum (SS) and septum primum (SP). These tissues (SS and SP) define a passage 114 that extends between the right and left atriums 102 and 104 and can be referred to as thick tissue 116 (SS) and thin tissue 118 (SP).

The thick tissue 116 forms the right margin of the passage 114 and comprises the superior portion of the interatrial septum 108. Thus, the thick tissue 116 extends upward and rightward away from the fossa ovalis 510. The thin tissue 118 forms the left margin of the passage 114 and comprises the inferior portion of the interatrial septum 108 (i.e., below the thick tissue 116) and extends upward and rightward substantially parallel to the thick tissue 116 and toward the left atrium 104.

Figure 2A:
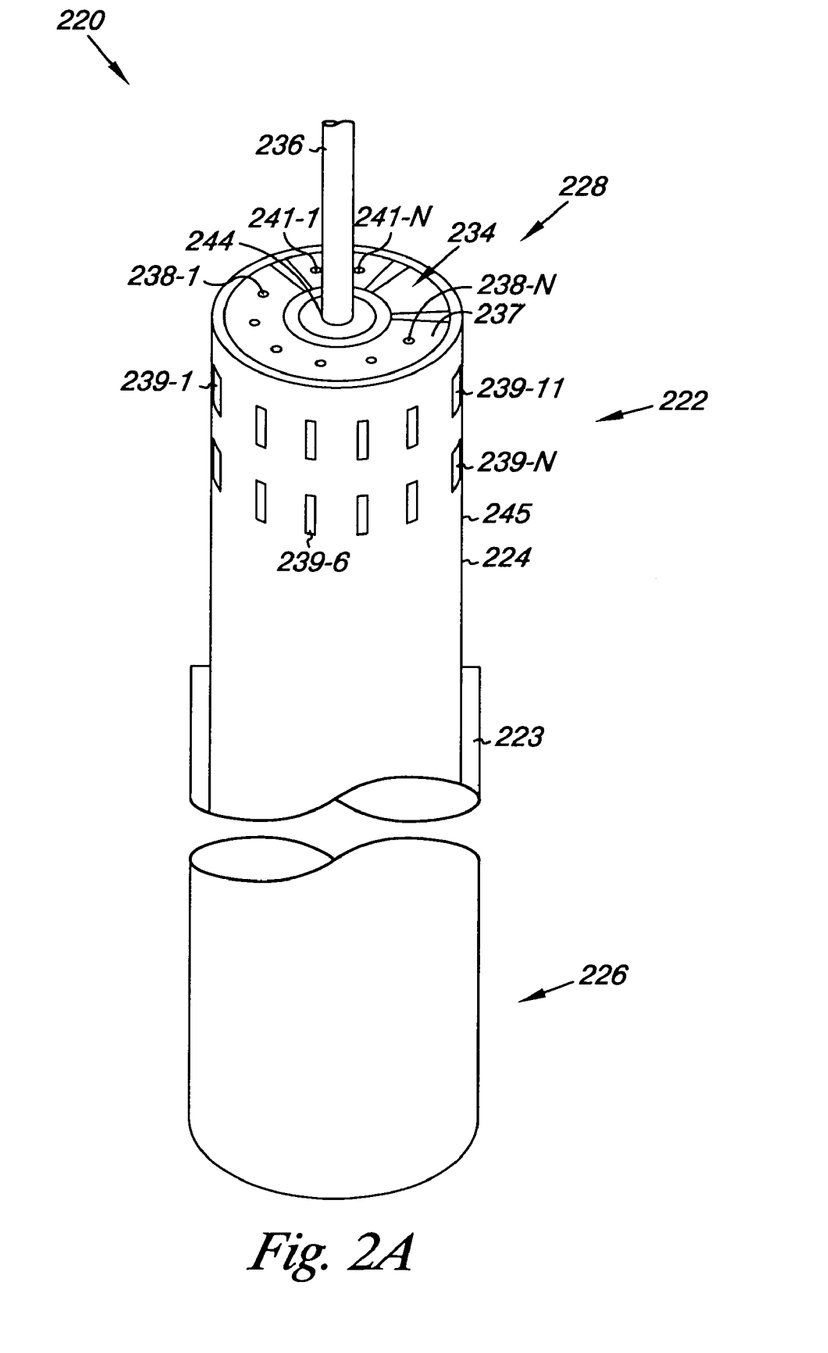
FIGS. 2A-2C illustrates embodiments of an occlusion apparatus according to the teachings of the present disclosure.
Figure 2B:
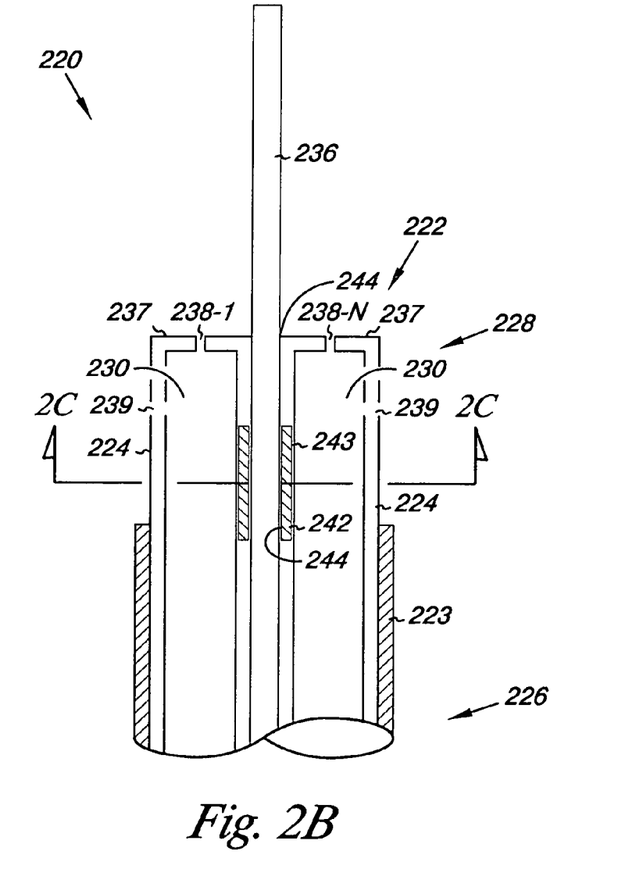
Figure 2C:
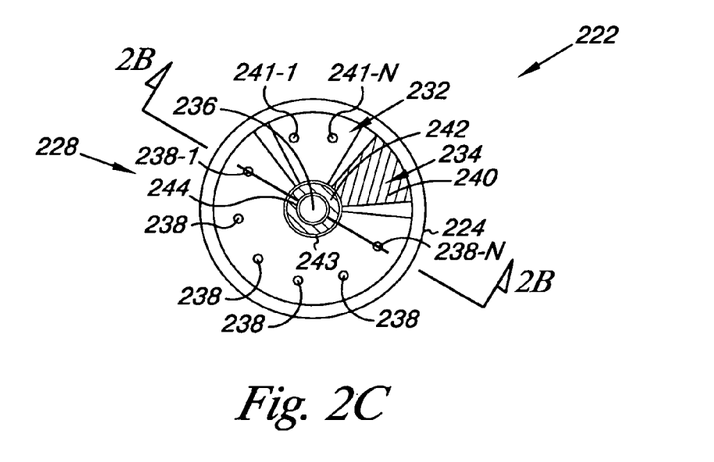

FIGS. 2A-2C illustrates various embodiments of an occlusion apparatus according to the teachings of the present disclosure. FIG. 2A illustrates a perspective view of the occlusion apparatus 220. FIG. 2B illustrates a cross-sectional view of the occlusion apparatus 220 along cut line B. FIG. 2C illustrates another cross-sectional view of the occlusion apparatus along cut line C. The various embodiments of the occlusion apparatus illustrated in FIGS. 2A-2C can include a varying number of components, lumens, substances, and functionalities. For example, in the embodiments illustrated in FIG. 2A, the occlusion apparatus 220 includes a catheter 222 having an elongate body 224 with a proximal end 226 and a distal end 228. In various embodiments, the catheter 222 can be slidably positioned within a sheath 223.

In various embodiments, the strength of the catheter 222 provides for pushability and resistance to buckling or kinking. In addition, the distal portion 228 of the catheter 222 can be formed of a more flexible material relative to the remaining portion of the catheter 222 to provide for the tracking of the catheter 222 over a guidewire through small tortuous vessels or body lumens to reach the fossa ovalis, as will be discussed below. Thus, in various embodiments, the catheter 222 can include elastomeric properties to improve flexibility along various portions of the elongate body 224 of the catheter 222.

Because catheter 222 will travel long distances within the vasculature of a patient to reach the fossa ovalis, the friction between a guidewire and the surface of a catheter lumen created by the tracking of the catheter over the guidewire can be minimized by constructing the catheter from a lubricious material such as a high-density polyethylene (HDPE), polytetrafluoroethylene (PTFE) or similar material. Polymeric materials are known for these uses.

In order to achieve a combination of desired properties at different parts of the catheter 222, the catheter can be formed by combining various types of polymeric materials having varying characteristics, e.g., various densities, fillers, crosslinking materials, etc. In various embodiments where the sheath 223 is utilized, the foregoing description of the properties of the catheter can also apply to the sheath 223.

In various embodiments, the elongate body 224 of the catheter 222 can include a number of lumens. Each lumen illustrated in the embodiments of FIGS. 2A-2C can extend from the proximal end 226 toward the distal end 228 of the elongate body 224. In various embodiments, each lumen can include an opening at the proximal end 226 and the distal end 228 of the elongate body 224. In addition, in various embodiments, lumens can include an opening defined by an outer surface of the lumen. In such embodiments, the lumens include a wall separate from a wall of the elongate body of the catheter, e.g., a catheter having a coaxial lumen design where an inner lumen is circumferentially surrounded by an outer lumen within the catheter, as will be discussed with respect to FIGS. 3A-3C.

In various embodiments, the lumens of the catheter can include various cross-sectional shapes, including, but not limited to, circular, ovular, polygonal, and irregular cross-sectional shapes. In some embodiments, the lumens can communicate with other portions of the catheter 222, e.g., a housing coupled to the distal end of the catheter, as will be discussed with respect to FIGS. 3A-3C.

As shown in the embodiments of FIGS. 2A and 2B, a first lumen 230 extends from the proximal end 226 toward the distal end 228 of the elongate body 224 of catheter 222. The first lumen 230 includes an opening at the proximal end 226 and the distal end 228 of the elongate body 224 of the catheter 222. At the distal end 228 of the catheter 222 and proximal to the distal end 228 of the catheter 222, the opening includes a number of ports 238-1 to 238-N and slots 239-1 to 239-N in fluid communication with the first lumen 230. As shown in FIG. 2A, the ports 238 are defined by an end surface 237 of catheter 222. And, the slots 239 are defined by an outer surface 245 of the elongate body 224 of the catheter 222. In various embodiments, the first lumen 230 can be filled with hypertonic saline and the hypertonic saline can be directed through the ports 238 and the slots 239 to tissue of the passage. In various embodiments, the ports 238 include a diameter not larger than 0.030 inches and not smaller than 0.010. In various embodiments, the slots 239 can include an area having a size not greater than 0.018 inches in width and at least 0.040 inches in length. The dimensions of each port 238 and each slot 239 are designed to provide an outlet for the flow of the hypertonic saline from the first lumen 230 to the surrounding tissue while substantially precluding tissue from entering the first lumen 230 under a vacuum generated by a vacuum member, as will be discussed below.

In various embodiments, the hypertonic saline can be 2% to 20% wt/volume. The hypertonic saline can include ions, for example, sodium phosphates, sodium bicarbonates, and sodium chlorides.

As shown in FIG. 2A, the elongate body 224 of catheter 222 can include a second lumen 232. Second lumen 232 extends from the proximal end 226 toward the distal end 228 of the catheter 222. In various embodiments, a vacuum member can be coupled to the second lumen 232 to provide a vacuum to the second lumen 232, as will be discussed in FIGS. 4-5D. In such embodiments, the second lumen 232 can be used to apply the vacuum through an opening in the second lumen 232 at the distal end 228 of the catheter 222. At the distal end 228 of the catheter 222, the opening includes a number of vacuum ports 241-1 to 241-N defined by end surface 237. The vacuum ports 241 communicate with the second lumen 232 such that a vacuum applied through the second lumen 232 and the vacuum ports 241 urges tissue at and proximal to the ports 241 toward the distal end 228 of catheter 222. As will be discussed in more detail below with respect to FIGS. 5A-5D, the vacuum can be applied to tissue of the passage (i.e., septum secundum and septum primum) to bring the tissue together.

In various embodiments of FIG. 2A, the vacuum can also be applied to the first lumen 230. In such embodiments, the fluidic ports 238 and slots 239 can function to both direct hypertonic saline through the fluidic ports 238 and slots 239 and to urge tissue toward the distal end 228 of the catheter 222 under the vacuum applied through the first lumen 230. To do this, hypertonic saline can be directed to tissue of the passage through the fluidic ports 238 and the slots 239 via the first lumen 230 to clear the area of blood at and proximal to the distal end 228 of the catheter 222. In such embodiments, the infusion of saline can be stopped and the vacuum can be applied through the first lumen 230 to urge the tissue toward the distal end 228 of the catheter 222 to bring the tissue together. In various embodiments, once the tissue contacts the distal end 228 of the catheter 222, some tissue can extend partially within the first lumen 230 via the fluidic ports 238 and slots 239 to form a seal between the outer surface 245 of the catheter 222 and the tissue. In such embodiments, a negative pressure created by the vacuum can be maintained on the tissue and thus, maintain the seal, by lowering a vacuum force of the vacuum. Lowering the vacuum force can allow an further infusion of hypertonic saline into the first lumen 230 to allow additional irrigation and covering of the tissues while the tissues are brought together to form the seal between the tissue and the outer surface 245 of catheter 222.

In various embodiments, the occlusion apparatus 220 can include a third lumen 234, as shown in FIGS. 2A and 2C. The third lumen 234 extends from the proximal end 226 toward the distal end 228 of the elongate body 234. As shown in FIG. 2C, the third lumen 234 can house a conductor 240 electrically coupled to a radiofrequency (RF) electrode 242. The conductor 240 can be formed of a variety of conductive materials. For example, the conductor 240 can be formed of metal such as stainless steel, copper, iron, aluminum, among others. In various embodiments, the conductor 240 can include an insulated sheath formed of polyimide and other insulating polymers.

In various embodiments, the third lumen 234 can also be used to accommodate additional conductors for electrically coupling other components of the occlusion apparatus 220. For example, conductors for electrically coupling sensors, such as temperature sensors and oxygen sensors can be positioned within the third lumen 234. In various embodiments, a conductor for electrically coupling a targeting device attached to the occlusion device 220 can also be housed within the third lumen 234, as will be discussed in more detail below with respect to FIG. 4.

In various embodiments, the occlusion apparatus 220 can include an RF electrode 242 coupled to the elongate body 224 proximal the distal end 228 of the elongate body 224, as shown in FIGS. 2B and 2C to form a circuit between the RF electrode 242, the conductor 240, and other components of the occlusion apparatus 220, as will be discussed in FIG. 4. In various embodiments, the RF electrode 242 can be configured to use monopolar or bipolar RF energy. In embodiments that use monopolar RF energy, the circuit can be completed through an external ground attached to the skin of the patient. In embodiments that use bipolar RF energy, the circuit can be completed through a ground attached to the occlusion apparatus 220.

In various embodiments, the hypertonic saline and the RF energy work together to facilitate a distribution of the RF energy along the tissue to fuse the tissue of the passage and to conduct RF energy through hypertonic saline covering tissue of the passage. Because hypertonic saline is conductive, it can help to distribute the RF energy across tissues covered by the hypertonic saline. In addition, the hypertonic saline can help to decrease the frequency and intensity of RF energy emitted from the RF electrode 242 that is necessary to denature the tissue of the passage.

In various embodiments, the RF electrode 242 can include a variety of shapes and can be formed of a variety of materials. For example, RF electrode 242 can be cylindrical, curved, planar, etc. In addition, the RF electrode 242 can include patterned surfaces such as a mesh, a weave, a lattice, etc. In the embodiment of FIGS. 2A-2C, the RF electrode 242 includes a cylindrical structure embedded within an inner wall of the elongate body of the catheter 220. In various embodiments, the RF electrode can be coupled to a surface of the elongate body, e.g., outer surface 245 of catheter 222 or an inner surface of the catheter, as shown in FIGS. 2B and 2C, and described below. In various embodiments, the RF electrode 242 can be coupled to the elongate body 224 using mechanical fasteners and/or chemical fasteners such as adhesives. In some embodiments, the RF electrode 242 can be coupled to the elongate body 224 by embedding the RF electrode 242 within a wall of the catheter. For example, in the embodiment illustrated in FIGS. 2B and 2C, the RF electrode 242 includes a cylindrical shape and is embedded within a wall 243 of a fourth lumen 244. In such an embodiment, the catheter 222 and the RF electrode 242 can be formed in a molding process, where the catheter 222 is overmolded to the RF electrode 242. In such embodiments, the catheter 222 can also be overmolded to the various conductors of the occlusion apparatus 220, e.g., RF electrode conductor 240, a sensor conductor, etc.

In various embodiments, the RF electrode 242 is coupled to the elongate body 224 at least 2 millimeters and at most 5 millimeters from the distal end 228 of the catheter 222. In various embodiments, the RF electrode 242 includes a surface area at least 20 mm$^2$.

In various embodiments, the fourth lumen 244 can extend from the proximal end 226 toward the distal end 228 of the catheter 222, as shown in FIGS. 2A and 2C. In various embodiments, the fourth lumen 244 can receive a receive a guidewire 236 over which the catheter 222 may be advanced to position the occlusion apparatus 220 within a heart chamber e.g., a left atrium of a patient, as will be discussed below with respect to FIGS. 5A-5D. In various embodiments, the guidewire 236 can include a number of components. For example, in various embodiments, the guidewire 236 can include a variety of sensors, e.g., temperature sensors such as thermocouples, oxygen sensors, etc., as will be discussed herein with respect to FIGS. 5A-5D.

Figure 3A:
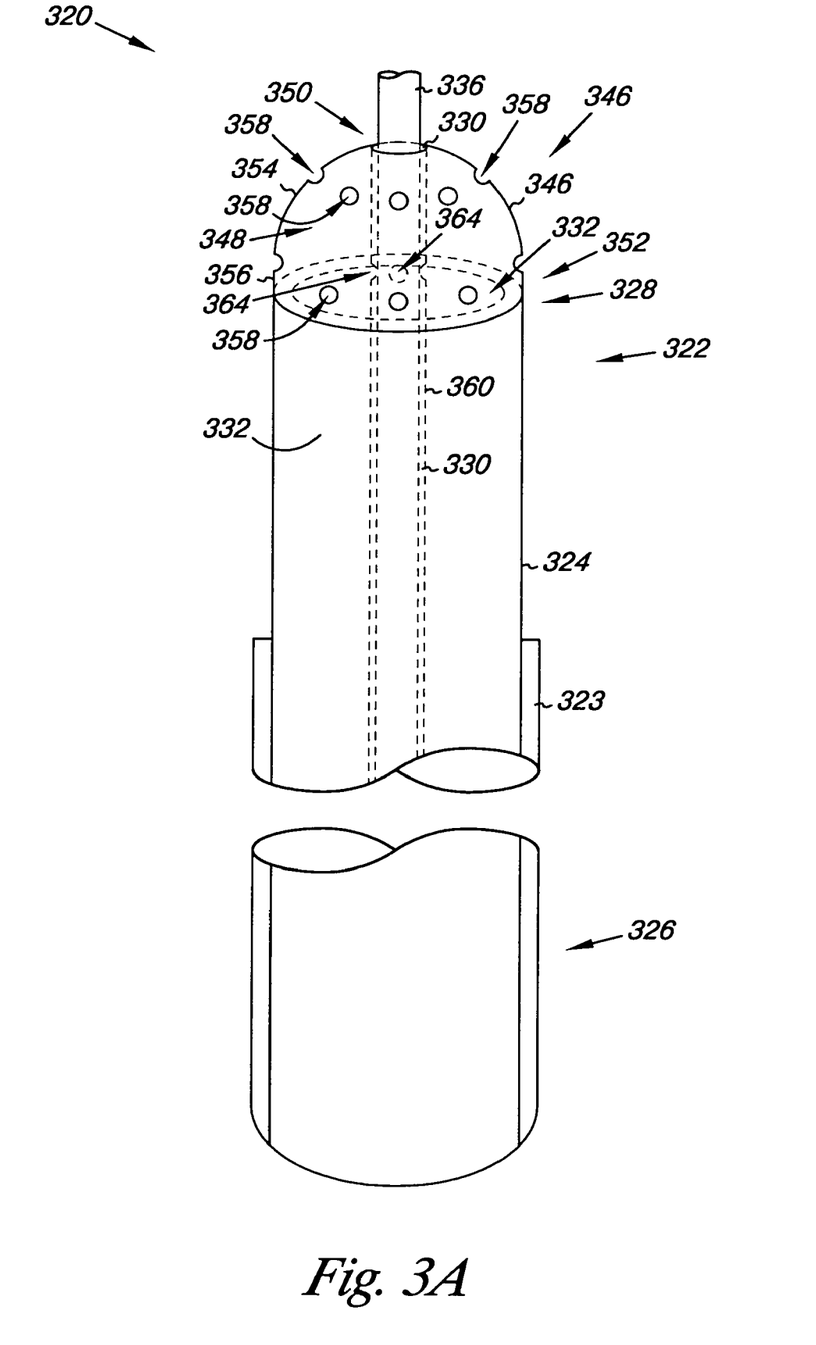
FIGS. 3A-3C illustrates another embodiment of an occlusion apparatus according to the teachings of the present disclosure.
Figure 3B:
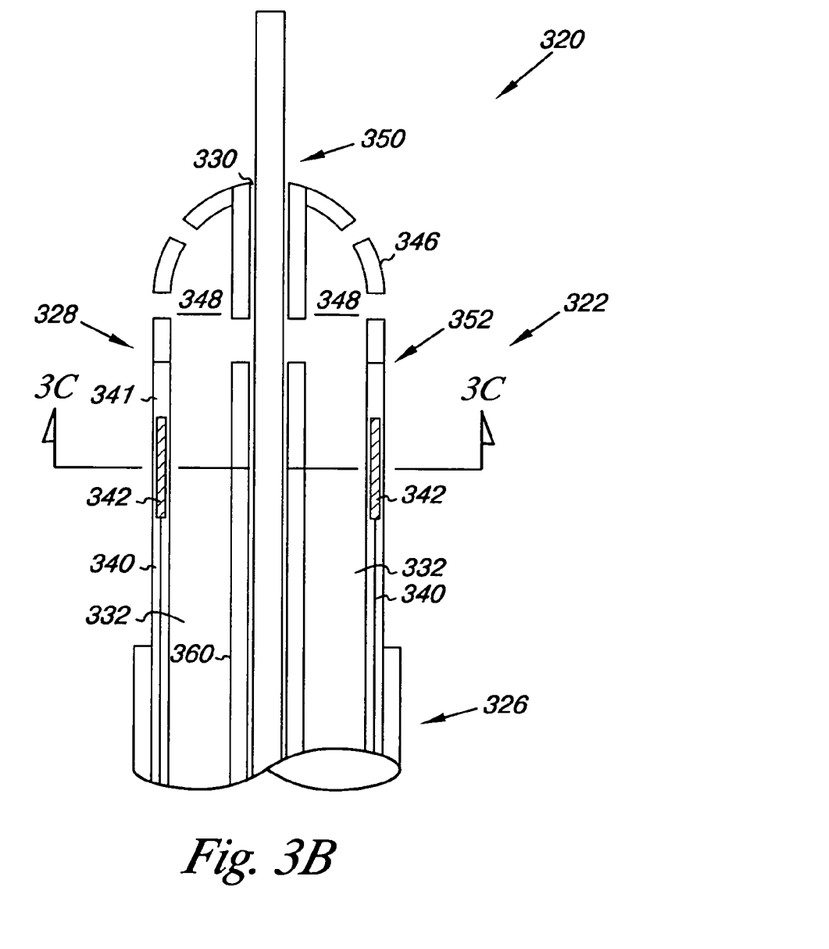
Figure 3C:
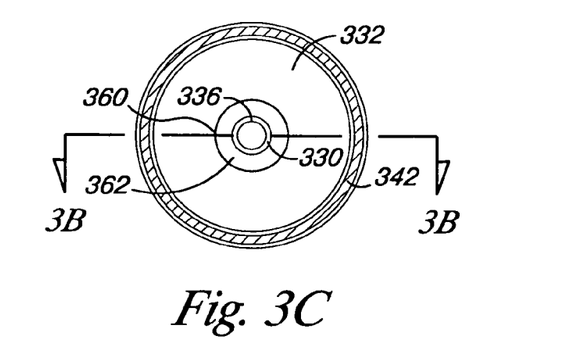

FIGS. 3A-3C illustrates another embodiment of the occlusion apparatus 320 of the present disclosure. FIG. 3A illustrates a perspective view of the occlusion apparatus 320. FIG. 3B illustrates a cross-sectional view of the occlusion apparatus 320 along cut line A. And FIG. 3C illustrates another cross-sectional view of the occlusion apparatus 320 along cut line C.

As shown in FIG. 3A, the occlusion apparatus includes the catheter 322 and sheath 323. In various embodiments, catheter 322 can include a housing 346 coupled to the distal end 328 of the catheter 322. As shown in FIG. 3A, the housing 346 includes a dome shape that defines a space 348 between the distal end 328 of the catheter 322 and a distal end 350 of the housing 346. In various embodiments, the space 348 defined by the dome shape is in communication with the first and second lumen 330 and 332 of the catheter 322. The housing 346 may be coupled to the catheter 322 at the distal end 328 of the catheter as shown in FIG. 3A or it may coupled to the catheter 322 proximal to the distal end 328. For example, in various embodiments, a proximal end 352 of the housing 346 can extend within the elongate body 324 of catheter 322 such that an outer surface 354 of the housing 346 couples to an inner surface of the second lumen 332 of the catheter 322. In various embodiments, the housing 346 and the catheter 322 can be formed as a unitary structure in a molding process or the housing 346 and the catheter 322 can be formed separately and coupled to each other using mechanical and/or chemical fasteners, as the same are known and understood by one of ordinary skill in the art. In various embodiments, the housing 346 can be formed of a metal, a metal alloy, and/or a polymer. Examples of suitable materials can include, but are not limited to, polymers such as plastics, thermoplastics, thermosetting plastics, etc. For example, in various embodiments, the housing can be formed of polypropylene, PTFE, ePTFE, PEEK, nylon, polyurethane, polyethylene, polyvinyl, saturated and unsaturated polyesters, phenolics, vinyl ester, silicone, urethane, etc. Housing 346 formed of metal or metal alloy can be insulated by an insulative polymer such as parilene and/or those listed above.

In various embodiments of FIGS. 3A-3C, the housing 346 can include a wall 356. In various embodiments, the wall 356 can include a solid material, a mesh material, a weave material, or a wire material or a combination of a solid, a mesh, a weave, and a wire material. In various embodiments, the wall 356 can be formed to include the housing openings 358, such as by forming the wall 356 of a mesh material, a weave material, and/or a wired material. In some embodiments, the housing openings 358 can be formed by stamping the housing openings 358 from a solid material or in a molding process where the housing openings 358 are formed in a mold. In the embodiment illustrated in FIG. 3A, the wall 356 is formed of a polymeric solid material and stamped to include the housing openings 358. In various embodiments, the housing openings 358 can include a diameter in a range of 0.010 mm to 0.040 mm, e.g., a range of 0.020 mm to 0.030 mm. In various embodiments, the size and placement of the housing openings 358 can be designed to enhance a structural integrity of the housing. For example, in various embodiments, the housing openings 358 can be formed an equal distance from each other in all directions so as to provide the wall 356 with a uniform stress resistance per unit area over the surface area of the wall 356. In addition, the wall 356 of the housing 346 can include an opening at the distal end 350 of the housing 346 to accommodate an extension and retraction of a guidewire 336, as will be discussed below. In various embodiments, the housing can include a height (i.e., a distance between the proximal end 352 and the distal end 350 of the housing 346) in a range of 1 mm to 5 mm, e.g., a range of 3 mm to 4 mm.

As shown in FIG. 3A, the catheter 322 includes a coaxial lumen design. That is, the catheter 322 includes a first lumen 330 defined by an elongate body 360 that extends from the proximal end 326 toward the distal end 328 of the catheter and is centrally positioned in the middle of the second lumen 332. The elongate body 360 of first lumen 330 includes an elongate body wall 362 that defines a number of wall openings 364 at varying locations between the proximal end 352 and the distal end 350 of the housing 346. The wall openings 364 are in fluid communication with the space 348 defined by housing 346. In various embodiments, the first lumen 330 can receive hypertonic saline and the hypertonic saline can be distributed to the space 348 via the wall openings 364 of the first lumen 330. In such embodiments, the hypertonic saline can then be directed to tissue of the passage via housing openings 358 defined by the wall 356 of housing 346.

In various embodiments, first lumen 330 can receive the guidewire 336 as discussed above with respect to FIGS. 2A-2C. In the embodiment of FIGS. 3A-3C, the guidewire 336 can have a diameter smaller than a diameter of the first lumen 330, as shown in FIGS. 3A-3C. In such embodiments, the guidewire 336 can be extended from the catheter 322 and retracted into the catheter 322 while allowing the hypertonic saline in the first lumen 330 to flow around the guidewire 336 and into the space 348 of housing 346 through the wall openings 364 of first lumen 330. In addition, the hypertonic saline can flow around the guidewire and exit the catheter 322 via the opening at the distal end 350 of the housing 346.

As shown in the embodiment of FIG. 3A, the second lumen 332 extends from the proximal end 326 toward the distal end 328 of the elongate body 324 of catheter 322. The second lumen 332 communicates with the space 348 defined by housing 346. In various embodiments, the second lumen 332 can be connected to a vacuum member to provide a vacuum through the second lumen 332, the space 348 defined by the housing 346, and the housing openings 358. When the housing 346 is positioned adjacent to or proximal to tissue of the passage, the vacuum urges the tissue toward the housing openings 358 to bring the tissue together, as will be discussed in more detail below with respect to FIGS. 5A-5D.

As shown in the embodiment of FIG. 3B, the occlusion apparatus 320 can include the RF electrode 342 as described with respect to FIGS. 2A-2C. As shown in FIG. 3B, the RF electrode 342 and a conductor 340 are embedded within an outer wall 341 of the elongate body 324 of catheter 322. In various embodiments, a portion of the housing 346 can serve as the RF electrode 342. In such embodiments, the housing 346 can be formed of a conductive material, such as stainless steel and the conductor 340 can be integrally formed with the housing 346.

Figure 4:
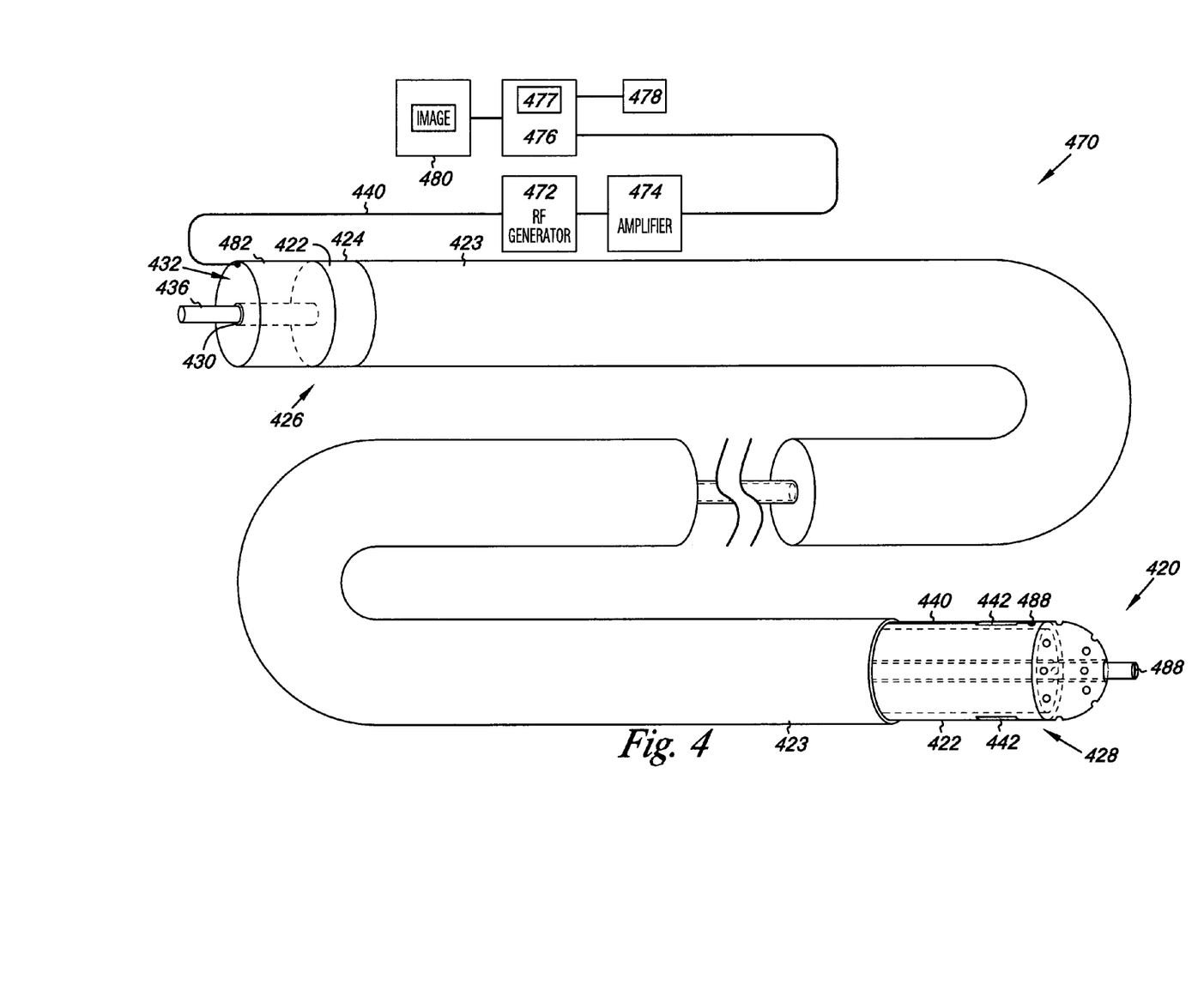
FIG. 4 illustrates an embodiment of a system of the present disclosure.

FIG. 4 illustrates an embodiment of a radio frequency occlusion system 470. In the embodiment illustrated in FIG. 4, an occlusion apparatus 420 as described in connection with FIGS. 3A-3C is illustrated. However, in various embodiments of FIG. 4, the occlusion apparatus 220 illustrated in FIGS. 2A-2C can also be used.

In various embodiments of FIG. 4, the system 470 can include a catheter 422 having a proximal end 426 and a distal end 428. As shown in FIG. 4, the catheter 422 includes a sheath 423, in which the catheter is slidably positioned. In various embodiments however, the system 470 can be utilized without the sheath 423. The catheter 422 includes a first lumen 430 and a second lumen 432, the first and second lumens 430 and 432 extending from the proximal end 426 toward the distal end 428 of the catheter 422. In various embodiments, a vacuum member 482 can be attached to the second lumen 432 at the proximal end 426 of elongate body 424 and can be operatively and communicatively coupled to other components of the system, e.g., power source, computer, targeting device, etc., as will be discussed below.

The catheter 422 can further include a guidewire 436. The guidewire 436 can extend within and along the length of an elongate body 424 of the catheter 422 from the proximal end 426 to the distal end 428 of the catheter 422 within the first lumen 430. In various embodiments, the guidewire 436 can be used to position the occlusion apparatus 420 within a heart chamber e.g., a left atrium of a patient.

In various embodiments, the system 470 can include the RF electrode 442, as the same has been described herein. The RF electrode 442 is operatively coupled to conductor 440, an RF energy generator 472, amplifier 474, a computer 476 including program instructions 477 (i.e., software) executable on the computer 476, a display 480, and a targeting device 478, etc.

As used herein, the targeting device 478 is a device that can create a target and/or locate a target to help deliver RF energy emitted from the RF electrode 442 to the target. As used herein, a target is a location to which RF electrode 442 delivers energy, for example, tissues of the passage. As used herein, creating a target means visually defining a target using the display screen 480 to display an image of tissue to which an operator can deliver RF energy and/or using software and a computer to define a target using trigonometric algorithms (e.g., triangulation), dynamic depth focusing algorithms, and the like, to which RF energy is to be delivered. And, as used herein, locating a target means visually observing a target using a display screen displaying an image of the target or displaying an image of tissue to which RF energy is to be delivered.

For example, in various embodiments, an ultrasound imaging screen 480 can be utilized by an operator to create a target by viewing tissue on a display screen and visually defining the area to be treated without the use of computers and software. In other embodiments, an operator can use the targeting device 478 including program instructions 477 executable on the computer 476 so that the target can be created on the ultrasound imaging screen 480 using a trigonometric algorithm, as discussed above.

In various embodiments, delivering the RF energy to the target can include utilizing the targeting device in conjunction with program instructions 477 executable on the computer 476 coupled to the targeting device 478 and/or RF electrode 442 to help a physician deliver the RF energy to the target. In various embodiments, delivering the RF energy to the target can include a manual process where the physician controls the direction of the RF energy, and other parameters such as frequency, intensity, temperature, and duration of the RF energy. In some embodiments, delivering the RF energy to the target can include an automated process where mechanical devices, such as robotic devices controlled by program instructions 477, delivers and directs the RF electrode and the RF energy emitted from the electrode including the frequency, intensity, temperature, and duration, among other parameters involved in operating the targeting device 478 and the RF electrode 442.

The various embodiments of the targeting device can be configured to provide real-time images of the target (e.g., a real time imaging ultrasound device, a real time MR imaging device, a real time optical imaging device, etc.). The real-time images can be provided before, during, and/or after the application of energy to the target. For example, in various embodiments, a targeting device that includes an imaging ultrasound device can be configured to provide real-time images of the target such that an operator of the energy emitting device can apply energy to the target while simultaneously viewing the target. Such embodiments allow the operator to verify that energy emitted from the energy emitting device is correctly guided to the target. Such embodiments also provide the operator with real-time monitoring of changes to tissues induced by the application of energy to the tissues.

The targeting device 478 can include a single component or multiple components. In addition, the components of the targeting device 478 can be located at a target, proximal to a target, and/or distal to the target. For example, in some embodiments, the targeting device 478 can include multiple components where one component is located adjacent the target, and another component is located distal to the target. For example, in various embodiments, the targeting device can include radiopaque markers as one component positioned at or proximal to the target and a display screen as another component can be positioned distal to the target and can provide an image of the radiopaque markers at or proximal to the target.

Examples of components of the targeting device can include, but are not limited to, imaging probes and devices (e.g., MR Imaging, ultrasound imaging), Doppler devices (e.g., Doppler audio), software, computers, dynamic depth focusing devices, and targeting markers (e.g., ultrasound targeting icons, radiopaque markers, and the like).

In various embodiments, the targeting device 478 can include other functions such as monitoring the tissue for physical changes, visual changes, thermal changes, and the like. For example, in various embodiments, an operator of the targeting device 478 can monitor the temperature of the tissues of the passage after RF energy has been applied to determine if the tissues have sufficiently cooled and whether they have fused together. For example, in various embodiments, the targeting device can include a monitoring function that provides thermometric imaging that can include a temperature map of the targeted area, as the same will be known and understood.

Multiple components can be employed in conjunction with the targeting device 478. For example, catheter 422 and/or guidewire 436 can include temperature sensors 488, such as thermocouples, attached to the distal end 428 of the catheter 422 and/or the distal end of the guidewire 436. In various embodiments, temperature sensors that are used in conjunction with controlling the RF energy are in contact with tissue that is denatured by the RF energy. Thus, in embodiments where temperature sensors 488 are coupled to the distal end of the guidewire 436, the distal end of the guidewire is in contact with tissue while RF energy is applied to the tissue to provide a monitoring and control function to the RF electrode, e.g., if temperature rises above a predetermined or set temperature, the RF electrode can be automatically or manually deactivated. In addition, temperature sensors coupled to the occlusion device 420 are positioned away from the flow path of the hypertonic saline, since the saline can have a tendency to interfere with an accurate temperature reading.

The various embodiments of the targeting device 478 can be configured to provide real-time images of the target (e.g., a real-time imaging ultrasound device, and a real-time MR imaging device). The real-time images can be provided before, during, and/or after the application of energy to the target. For example, in various embodiments, a targeting device that includes a real-time imaging ultrasound device can be configured to provide real-time images of the target such that an operator of the RF electrode can apply energy to the target while simultaneously viewing the target, as the same are known in the art. Such embodiments allow the operator to verify that energy emitted from the RF electrode is correctly delivered to the target. Such embodiments also provide the operator with real-time monitoring of changes to tissues induced by the application of energy to the tissues while the energy is being applied to the tissues.

FIGS. 5A-5E illustrate embodiments of methods for fusing tissues of the passage by bringing tissues of the passage together and fusing the tissues with RF energy emitted from the RF electrode.

Figure 5A:
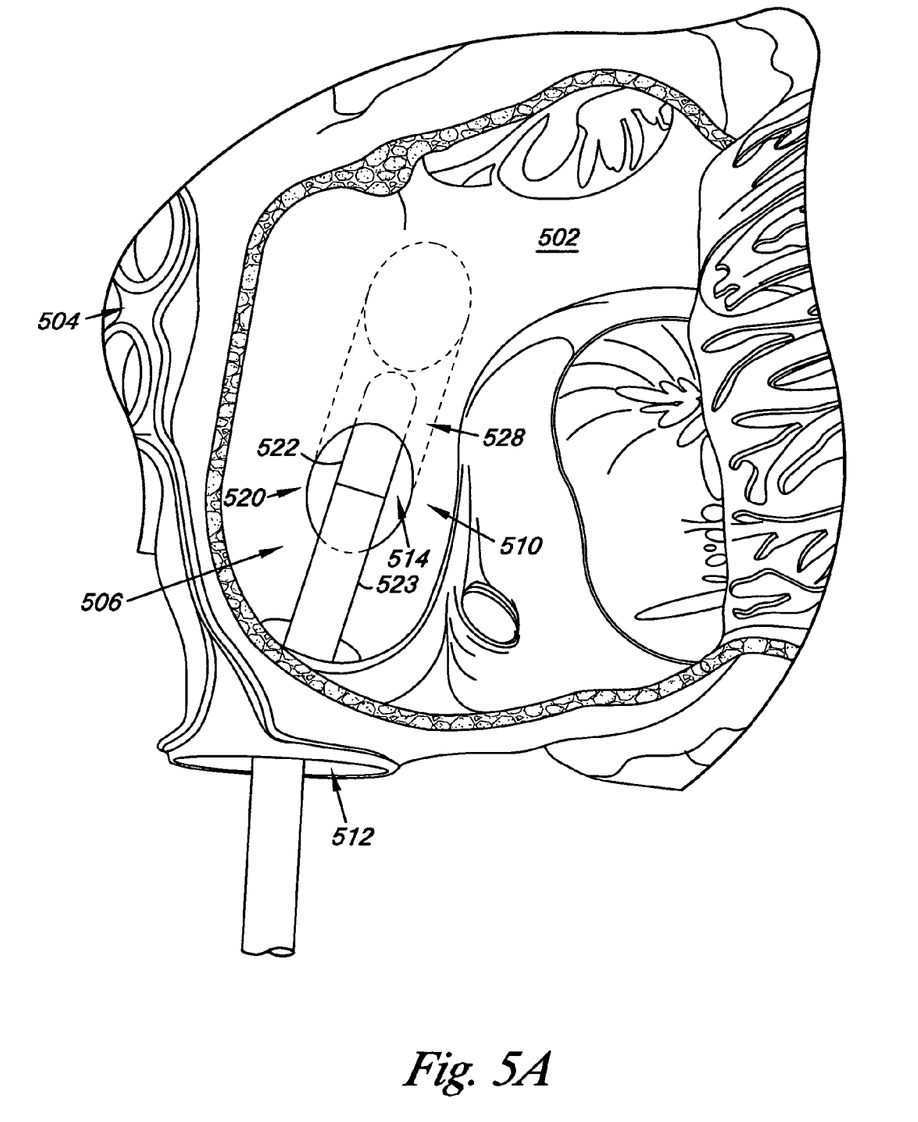
FIG. 5A-5D illustrates various embodiments of a method for fusing tissue of the passage.

As shown in FIG. 5A, the tissue adjacent the fossa ovalis 510 (e.g., SS and SP) can be accessed in a number of ways as will be apparent to those skilled in the art. For example, in various embodiments, catheter 522 can be positioned within the right atrium 502 by introducing the catheter 522 into the venous system of the patient using a minimally invasive percutaneous, transluminal catheter based delivery system. For example, the guidewire, as described herein, can be positioned within the venous system and advanced to the right atrium 502 of a patient. In various embodiments, the right atrium 502 can be entered via the orifice of the inferior vena cava 512. The catheter 522 can be positioned over the guidewire and the catheter advanced so as to position the distal end 528 of the catheter 522 at or adjacent the septal wall 506 of right atrium 502. A unique aspect of the fossa ovalis 510 is its location relative to the orifice of the inferior vena cava 512. Since the fossa ovalis 510 is located above and to the left of the orifice of the inferior vena cava 512, the catheter 522 can be immediately advanced to the fossa ovalis by the use of the guidewire upon entering the right atrium 502 from the orifice of the inferior vena cava 512. In various embodiments, radiopaque markers on the catheter 520 can be used to help to visualize and position the catheter 520 within the right atrium 502 and proximal to or adjacent the fossa ovalis 510, as discussed herein. In addition, orientation and visualization of the catheter may be accomplished through the use of any combination of MR imaging, echogenic, angioscopic, imaging ultrasound, and fluoroscopic visualization techniques.

Once the physician has properly positioned the distal end 528 of the catheter 522 adjacent the fossa ovalis 510, the physician can advance a portion of the catheter 522 within the passage 514 (e.g. between thick and thin tissue 116 and 118). A radiopaque or radiographic contrast media, e.g., radiografin, may then be injected through a lumen of the catheter or guidewire to allow visualization and ensure that the location of the catheter 522 is within the passage 514, as opposed to other locations, e.g., the aorta. In some embodiments, an oxygen sensor coupled to the guidewire can be used to determine the proper location of the catheter. For example, the guidewire can be advance through the passage 514 to access the left atrium 504. Because blood in the left atrium 504 is saturated with oxygen, having been oxygenated by the lungs, an oxygen sensor coupled to the distal end of the guidewire can determine whether or not the guidewire is positioned within the left atrium and thus, confirm that catheter is properly positioned within the passage 514.

The embodiment of FIGS. 5B-5E illustrates in more detail the method for fusing tissues of the passage 514. The occlusion apparatus 520 illustrated in the embodiments of FIGS. 5B-5E includes the embodiment of the occlusion apparatus 320 illustrated in FIGS. 3A-3C. In various embodiments however, the occlusion apparatus illustrated in FIGS. 2A-2C can also be used to fuse tissue of the passage.

Figure 5B:
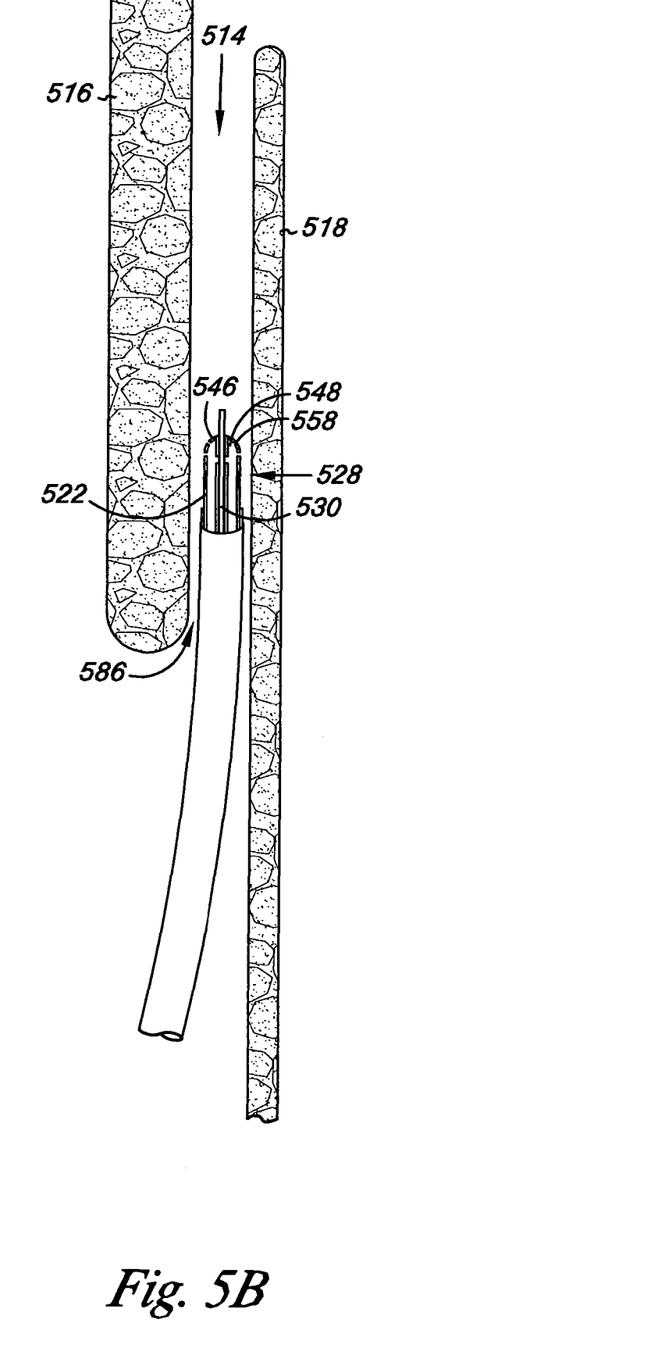

As shown in FIG. 5B, one method for fusing tissue of the passage can include positioning the distal end 528 of the catheter 522 within the passage 514, as shown in FIG. 5B. Once the distal end 528 of the catheter 522 is properly positioned, the surfaces of the tissue forming the passage (thick tissue 516 and thin tissue 518) at and proximal to the distal end 528 of the catheter 522 can be covered with hypertonic saline. In various embodiments, 1-10 milliliters of hypertonic saline should be sufficient to cover the tissue to be treated by the RF energy. In various embodiments, covering surfaces of the tissue can help to irrigate blood away from the distal end of the catheter and away from the area of tissue to which RF energy is emitted. Irrigating blood away from the area of tissue to which RF energy is emitted can prevent unwanted blood clotting that can result from the heat produced by the RF energy. In various embodiments, the hypertonic saline may be circulated through the space 548 defined by housing 546 to clear the space 548 of blood and tissue that may enter the housing or partially enter the housing through the housing openings, as described herein. For example, hypertonic saline may be circulated by introducing the hypertonic saline to the housing 546 from the first lumen 530 and then using the vacuum to bring the fluid back into the first lumen 530. In some embodiments, a fluid lock, as is known in the art, can be coupled to the catheter at the proximal end of the catheter to prevent the extraction of fluid from the patient. In various embodiments, covering the tissue of the passage can include directing the hypertonic saline to the surfaces of tissue at and proximal to the distal end 528 of the catheter 522. In various embodiments, the hypertonic saline that covers the tissue can include a % weight/volume range of 2% wt/volume to 20% wt/volume.

Figure 5C:
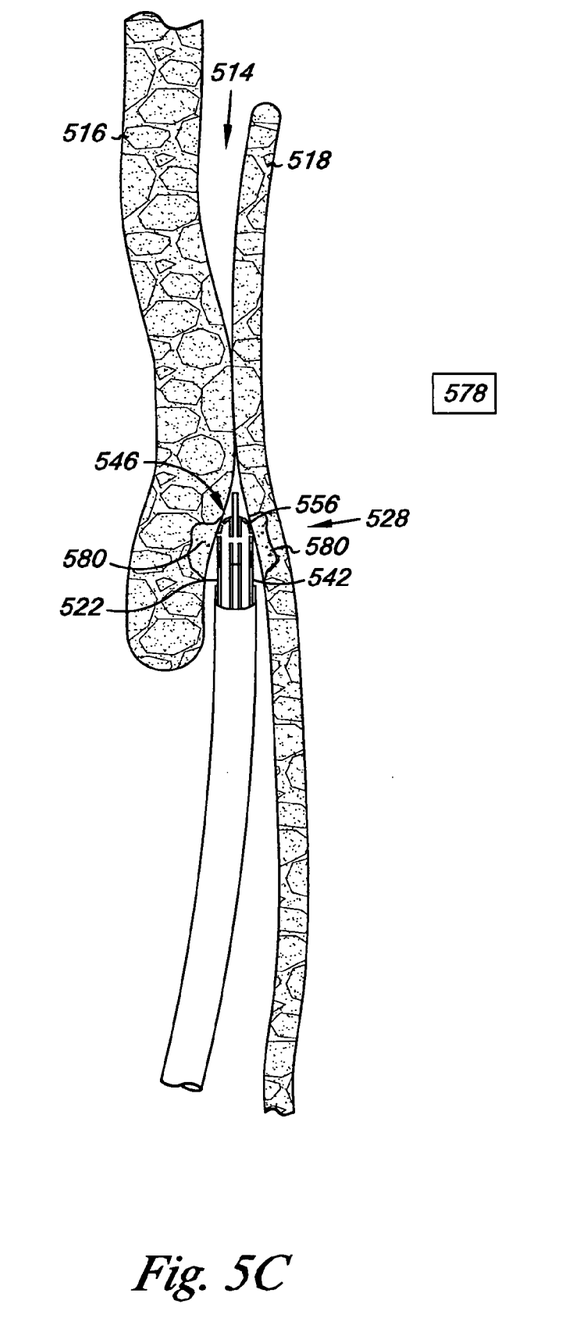

As shown in FIG. 5C, once the tissue has been sufficiently covered with the hypertonic saline and the area around the tissue has been substantially cleared of blood, the vacuum, as discussed in FIG. 4, can be applied to the tissue to appose the tissue forming the passage 514, i.e., thick tissue 516 and thin tissue 518. In various embodiments, the vacuum urges tissue at and proximal to the distal end 528 of the catheter 522 toward the catheter 522. In various embodiments, the distal end 528 of the catheter 522 can be manipulated such that it contacts thick or thin tissue 516 and 518. For example, in various embodiments, the distal end 528 of the catheter 522 can be positioned adjacent the thin tissue 518 such that it contacts the thin tissue 518. The vacuum can then be applied to the thin tissue 518 to urge the tissue against the wall 556 of the housing 546. In such an embodiment, the distal end 528 of the catheter 522 can then be moved toward the thick tissue 516 while maintaining the vacuum so as to bring the thin tissue 518 toward the thick tissue 516. The vacuum can then act on the thick tissue 516 to bring the thick and thin tissue 516 and 518 together such that they contact each other and form a seal between the tissue and the outer surface of the occlusion device, as discussed above with respect to FIGS. 2A-2C.

In various embodiments, the method for fusing the tissue of the passage can be monitored to ensure that tissue has been properly apposed before fusing the tissue with RF energy. For example, in various embodiments, various sensors for detecting blood within the occlusion apparatus, e.g., the housing, various lumens of the device, and vacuum member can be employed. In some embodiments, a temperature sensor can be employed to measure the temperature of fluid within the occlusion apparatus. The temperature of blood will include a range of 96.8° to 99.5° F. (36-37.5° C.), wherein the temperature of the hypertonic saline will be considerably lower. In various embodiments where the temperature falls within the range of 96.8° to 99.5° F., the vacuum can be shut off or the vacuum force can be reduced and hypertonic saline can be reintroduced to further irrigate blood from the tissue until a seal between the tissue and the outer wall at the distal end of the catheter has been achieved. In some embodiments, the color of the fluid within the occlusion apparatus can be monitored using an optical sensor coupled to the occlusion apparatus. The optical sensor can be used to detect blood within the occlusion apparatus.

In various embodiments, once the tissues are brought together using any of the methods described above, RF energy can be applied to the tissues. In various embodiments, the method for fusing tissue of the passage can include applying RF energy to tissues with the RF electrode to substantially occlude the opening of the PFO at the location of the fossa ovalis 510.

For example, in various embodiments, RF electrode 542 can deliver RF energy to the tissues at a target 580, e.g., the location in which the occlusion device 520 brings the tissues together. In various embodiments, the RF energy can include a frequency in a range of 300 KHz to 5 MHz, intensity in a range of 1 to 10 Watt/cm$^2$, and duration of about 5 to 35 seconds.

Figure 5D:
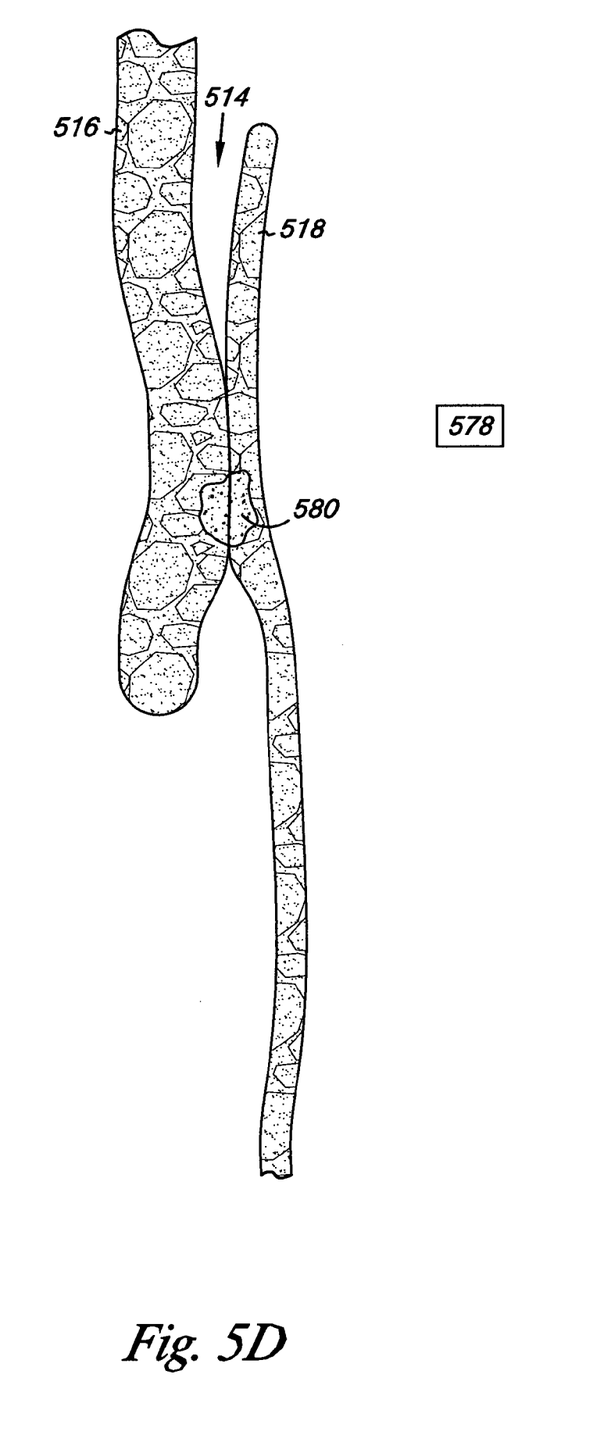

As shown in FIGS. 5C and 5D, the RF energy causes ionic agitation, and therefore friction, in the tissue. This friction creates heat, and once sufficient temperatures have been reached, the heat denatures the tissue. Once the tissue has sufficiently denatured, the emission of RF energy is stopped and the tissue begins to cool. In various embodiments, tissue that is in contact with other tissue when it is denatured, will fuse together when the tissue cools and begins to renature. In various embodiments, the level of frequency, intensity, and the duration of RF energy applied to the tissue of the passage and the resistance of those tissues can dictate the size of the area of tissue that is denatured because the heat produced from the RF energy decreases rapidly at a specific distance from the RF electrode. Thus, the size of the denatured area is determined largely by the size of the electrode, the temperature of the tissue, and the duration of time the RF energy is applied. There is a clearly delineated border between denatured tissue and unaffected surrounding tissue. Thus tissue can be fused together without much sacrifice to the surrounding non-fused tissue.

As discussed herein, once the tissues are denatured, the tissues begin to renature and fuse together as they cool. In various embodiments, the process can be repeated to fuse the tissue at other targets, i.e., other locations in which tissue is brought together such that it contacts each other, if the operator so desires. As discussed herein, the targeting device 578 described in FIG. 4, can be used to create and/or locate the target 580. In addition, the targeting device can be used to help deliver the RF energy to the target 580 using imaging ultrasound, MR imaging, and other components of the targeting device. Once the targeted tissues of the passage 514 are sufficiently denatured, the operator can deactivate the RF electrode and wait for the tissues to cool.

As shown in FIG. 5D and as discussed herein, when the thick and thin tissues 516 and 518 of the passage have sufficiently cooled, they begin to renature and fuse together. An operator of the targeting device 578 can monitor the thick and the thin tissues 516 and 518 for changes (e.g., change in temperature) to determine if the tissues have sufficiently cooled and whether they have fused together at and proximal to the target 580. As discussed herein, monitoring of the tissue can be performed with the targeting device and/or sensors coupled to the catheter, e.g., temperature sensors. When the operator is satisfied that tissues are sufficiently cooled and renatured, e.g., fused together, the operator can stop the vacuum to release the tissue from the occlusion apparatus. Once released, the occlusion apparatus can be removed from the human body.

While the present disclosure has been shown and described in detail above, it will be clear to the person skilled in the art that changes and modifications may be made without departing from the scope of the invention. As such, that which is set forth in the foregoing description and accompanying drawings is offered by way of illustration only and not as a limitation. The actual scope of the invention is intended to be defined by the following claims, along with the full range of equivalents to which such claims are entitled.

In the foregoing Detailed Description, various features are grouped together in several embodiments for the purpose of streamlining the disclosure. This method of disclosure is not to be interpreted as reflecting an intention that the embodiments of the invention require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. An occlusion apparatus, comprising:
a catheter having an elongate body with a wall, distal end and a proximal end, the elongate body defining:
   a first lumen including surfaces that define openings from the first lumen through the elongate body wall and a distal end surface, the first lumen being configured to direct saline through the openings,
   a second lumen including surfaces that define second openings from the second lumen through the distal end surface to apply vacuum to the second openings,
   a third lumen enclosing an electrical conductor, and
   a fourth lumen located coaxially in the elongate body and enclosing a guidewire; and
a radiofrequency (RF) electrode coupled to the electrical conductor, located proximal the distal end of the elongate body and housed within the elongate body that defines the fourth lumen, wherein the openings are arranged and configured through the elongate body wall and distal end surface to deliver saline in a manner that displaces blood around tissue drawn to the distal end surface by vacuum applied through the second openings, the RF electrode located to distribute RF energy across the tissue through an enhanced conductive path established by the saline, where the catheter is configured to simultaneously conduct RF energy, direct saline solution through the openings through the elongate body wall, and apply vacuum to the second openings through the distal end surface.

2. The occlusion apparatus of claim 1, where the fourth lumen includes a distal opening that accommodates an extension and retraction of the guidewire.

3. The occlusion apparatus of claim 2, where the distal opening has a diameter in a range of 0.020 inches to 0.030 inches.

* * * * *